United States Patent [19]

Smith, Jr.

[11] 4,336,407

[45] * Jun. 22, 1982

[54] CATALYTIC DISTILLATION PROCESS

[75] Inventor: Lawrence A. Smith, Jr., Bellaire, Tex.

[73] Assignee: Chemical Research & Licensing Company, Houston, Tex.

[ * ] Notice: The portion of the term of this patent subsequent to Dec. 22, 1998, has been disclaimed.

[21] Appl. No.: 234,653

[22] Filed: Feb. 17, 1981

Related U.S. Application Data

[60] Continuation-in-part of Ser. No. 124,433, Feb. 25, 1980, which is a division of Ser. No. 13,559, Feb. 21, 1979, Pat. No. 4,232,177.

[51] Int. Cl.³ .................................................. C07C 41/06
[52] U.S. Cl. .................................. 568/697; 568/579; 568/672; 568/678; 203/DIG. 6
[58] Field of Search ............... 568/697, 579, 678, 672; 203/DIG. 6

[56] References Cited

U.S. PATENT DOCUMENTS

| | | |
|---|---|---|
| 2,403,672 | 7/1946 | Matuszak . |
| 3,091,586 | 5/1963 | Pappas et al. . |
| 3,121,124 | 2/1964 | Verdol . |
| 3,170,000 | 2/1965 | Verdol . |
| 3,270,081 | 8/1966 | Verdol . |
| 3,317,593 | 5/1967 | Enk et al. . |
| 3,531,539 | 9/1970 | Tidwell . |
| 3,629,478 | 12/1971 | Haunschild . |
| 3,634,534 | 1/1972 | Haunschild . |
| 3,726,942 | 4/1973 | Louder . |
| 3,825,603 | 7/1974 | Massie . |
| 3,846,088 | 11/1974 | Brown et al. . |
| 3,940,450 | 2/1970 | Lee . |
| 4,100,220 | 7/1978 | Bowman et al. . |
| 4,198,530 | 4/1980 | Wentzheimer et al. . |
| 4,232,177 | 11/1980 | Smith .................................. 568/697 |

OTHER PUBLICATIONS

Scheeline et al. Methyl Tertiary Butyl Ether, Process Economics Reviews SRI International, Menlo Park, Calif.

*Primary Examiner*—Howard T. Mars
*Attorney, Agent, or Firm*—Kenneth H. Johnson

[57] ABSTRACT

A method for conducting chemical reactions and fractionation of the reaction mixture comprising feeding reactants to a distillation column reactor into a feed zone and concurrently contacting the reactants with a fixed bed catalytic packing to concurrently carry out the reaction and fractionate the reaction mixture.

For example, a method for preparing methyl tertiary butyl ether in high purity from a mixed feed stream of isobutene and normal butene comprising feeding the mixed feed stream to a distillation column reactor into a feed zone at the lower end of a distillation reaction zone, and methanol into the upper end of said distillation reaction zone, which is packed with a properly supported cationic ion exchange resin, contacting the $C_4$ feed and methanol with the catalytic distillation packing to react methanol and isobutene, and concurrently fractionating the ether from the column below the catalytic zone and removing normal butene overhead above the catalytic zone.

48 Claims, No Drawings

CATALYTIC DISTILLATION PROCESS

The Government of the United States of America has certain rights in this invention pursuant to Contract No. DE-FC07-80CS40454 awarded by the U.S. Department of Energy.

This application is a continuation-in-part of Ser. No. 124,433 filed Feb. 25, 1980 which was a division of Ser. No. 013,559 filed Feb. 21, 1979 now U.S. Pat. No. 4,232,177.

BACKGROUND OF THE INVENTION

1. Field of the Invention

The present invention relates to a new method of conducting catalytic chemical reactions wherein separation of materials in the reaction mixture, i.e., product(s), by-product(s) or starting material(s) may be obtained by concurrent distillation or fractionation thereof.

One species of the present invention relates to the preparation of methyl tertiary butyl ether from streams containing mixtures of an isobutene and normal $C_4$ olefin. The present invention is especially useful for the separation of isobutene from streams containing n-butenes.

2. Description of the Prior Art

Isoolefins of 4 carbon atoms are difficult to separate from the corresponding normal olefin by simple fractionation because of the closeness of their boiling points. In prior art processes as generally practiced commercially, the isoolefin is selectively absorbed by sulfuric acid and the resulting isoolefin-containing sulfuric acid extract is then diluted and heated or treated with steam to separate the isoolefin.

The isoamylene is similarly difficult to separate from streams containing normal $C_5$ olefins.

The n-butenes are required in pure form for homopolymerization and as feeds for the oxidative production of butadiene. One manner of separating these components is to pass the mixture through what is called a cold acid extraction procedure wherein the stream is fed into a bath of concentrated sulfuric acid. Separation is achieved by virtue of the solubility of the isobutene in the sulfuric acid, the n-butenes and other hydrocarbons present passing overhead.

Methyl tertiary butyl ether (MTBE) has gained a wide acceptance as a non environmentally harmful octane improver for gasolines. One method of separating isobutene or isoolefins in general from mixtures with the corresponding normal olefins and alkanes, has been to etherify the isoolefin with a $C_1$ to $C_6$ primary alcohol in the presence of an acidic cation exchange resin catalyst, separate the low boiling hydrocarbons from the higher boiling ether by fractionation, frequently followed by decomposition of the ether to recover the isoolefin. Such procedures are disclosed in U.S. Pat. No.'s 3,121,124; 3,270,081 and 3,170,000.

More recently, in view of the ether octane improving characteristics, similar processes have been disclosed for preparing and recovering the ether, e.g., U.S. Pat. No.'s 3,726,942 and 3,846,088.

In a variation on these processes disclosed in U.S. Pat. No.'s 3,629,478 and 3,634,534 to Haunschild, the mixture of isoolefin and normal olefin with lower primary alcohols is fed to distillation column in which there are a plurality of zones of acidic ion exchange resin catalyst whereby the isoolefin ether is formed and drops to the bottom of the column while the normal olefins (and paraffins) are distilled overhead. In particular, the catalyst is contained in downcomers where the reaction is to occur and the distillation takes place on the trays of the column.

SUMMARY OF THE INVENTION

In the broader aspect of the present invention, a new method of carrying out chemical reactions wherein the materials of the reaction mixture are separated by distillation is disclosed. The process is contemplated to be used with reactants, products and inerts which are liquid or gaseous under the conditions of the reaction. The reactants may be a single material, such as isobutylene which reacts with itself to form diisobutylene in a $C_4$ stream containing normal butenes, wherein the normal butenes are recovered as an overhead and the diisobutylene recovered as bottoms (U.S. Pat. No. 4,242,530 granted to Lawrence A. Smith, Jr., which is incorporated herein) or the reactants may be different materials such as isobutene and methanol described in more detail herein. In any event, it is the discovery of the use of the catalytic material as both the catalyst and the distillation packing such that reaction and distillation are occurring concurrently in the fixed catalyst bed, which is the basis of new discovery.

One particular aspect of the present invention is the production of ethers from $C_4$ and $C_5$ olefins, both normal olefins and isoolefins, particularly where the olefins are components of streams containing alkanes such as $C_4$ and $C_5$ refinery streams or as a means to separate the isoolefins from the normal olefins.

Thus, the catalyst packing is of such a nature as to allow the vapor flow through the bed, yet provide a sufficient surface area for catalytic contact. In the process described in the earlier mentioned Haunschild patents, the catalyst is packed into the downcomers and maintained in what is a flooded state as the liquid in the column passes down through the downcomer to the next lower tray. The material from the downcomer is then fractionated on the lower tray as in a conventional tower.

For example, according to the present invention a higher boiling reactant is continually contacted with the catalyst and lower boiling reactants passing upward in the fixed catalyst bed which provides more opportunity for reaction. Similarly, the removal of a reaction component from the reaction mixture of a reversable reaction, forces the reaction to completion. Thus, in procedures where catalytic reaction and fractionation are features, the present process provides both functions in a single step. The equipment is very simple, and can utilize any type of distillation tower (provided the fixed beds of catalyst can be inserted therein to fill the reaction-distillation zone, It can be appreciated that any packing will restrict the vapor flow in the column and that if alternate unpacked avenues of travel are provided, the vapor will follow the route of least resistance. Thus, in a reactor configuration such as shown in the Haunschild patents, no vapor contact of flow could or would proceed through the catalyst packed downcomers.

The present process is also useful for reacting one material in a multicomponent feed and concurrently separating unreacted components of the feed therefrom by fractionation, as illustrated in U.S. Pat. No. 4,242,530, noted above.

The fractionation may be directed to recovering a product overhead or as a bottom fraction. It may also be directed to recovering a non reactant such as n-butene from the reaction mixture of isobutene and methanol, the n-butene being a feed stream component which is otherwise difficult to separate from the isobutene. Thus, the present disclosed process may be used for specific reactions between relatively pure reactants or the selective reaction and recovery of desired products from mixed feeds.

It is to be expected that for any particular feed stream and selective reaction therein, the specific conditions of reaction will need to be determined by some minimum amount of experimentation employing the invention as described herein and using information provided herein to conduct the process in accordance with the present invention. Similarly, although the illustration are primarily directed to mixed $C_4$ streams wherein isobutene is selectively reacted, other streams and processes are contemplated, as for example isomerizations of butene-2 to butene-1 and the concurrent fractionation of the resulting isomerization mixture. Furthermore, in addition to dimerization, etherification and isomerization, all other types of reactions are contemplated within the scope of the process, for example, esterification, chlorination, hydration, dehydrohalogenation, alkylation, polymerization, and the like.

The reactants (and inerts) are generally organic compounds (although some inorganic compounds may be dissolved therein). Although $C_4$ hydrocarbons are illustrated, it is contemplated that organic compounds which are fluid and produce reaction products which are subjected to fractionation for separation or recovery of materials from the reaction are all suitable for use in the present process.

Thus, in its generic form, the present invention is a method for concurrently conducting chemical reactions to produce a reaction mixture and fractionation of the reaction mixture comprising:

(a) feeding reactants to a distillation column reactor into a feed zone, (b) concurrently:

(1) contacting said reactants with a fixed bed catalyst packing in a distillation-reaction zone, thereby catalytically reacting said reactants to form a reaction mixture, (2) fractionating the resulting reaction mixture in said fixed bed catalyst to recover a lower boiling fraction of said reaction mixture overhead and a higher boiling fraction thereof as a bottom, whereby said reaction and fractionation are occurring concurrently witin the fixed catalyst bed which serves as both catalyst and distillation packing in said distillation column reactor.

DETAILED DESCRIPTION OF THE INVENTION AND SPECIFIC EMBODIMENTS

The catalytic material may be any material, appropriate for the reaction at hand, that is, it may be an acid catalyst or a basic catalyst or others such as catalytic metals and their oxides or halides suitable for a multitude of catalytic reactions and of course, heterogeneous with the reaction or other fluids in the system.

For example, a different reaction is the preparation of formic acid from methanol using iron oxide or transesterification using a base catalyst such as NaOAl.

The term "catalyst" or "catalytic material" is used to include any solid material which is recognized for the reaction under consideration as performing as a catalyst therein. Furthermore, the catalytic material must be in a form to serve as a distillation packing, for example, rings, saddles, balls, irregular pieces, sheets, tubes, spirals, packed in bags (as described in U.S. Pat. No. 4,242,530), plated on grills or screens, or reticulated polymer foams (the cellular structure of the foams must be sufficiently large so as not to cause high pressure drops through the columns or otherwise arranged, such as in chunks or concentric tubes to allow vapor flow). Broadly stated, the catalytic material is a component of a distillation system functioning as both a catalyst and distillation packing, i.e., a packing for a distillation column having both a distillation function and a catalytic function.

In one embodiment the present invention is a process for reacting $C_4$ and $C_5$ olefins with $C_1$ to $C_6$ alcohols to produce the corresponding ethers. The iso $C_4$ and iso $C_5$ olefins are more reactive than the normal corresponding olefins and can be removed in substantially quantitative amounts from $C_4$ and $C_5$ streams in which they are components. The $C_4$ and $C_5$ olefins may be in a single stream, however, normally these streams are separated and the stream to be contacted with the alcohol is substantially a $C_4$ or $C_5$ stream containing only minor amounts of other hydrocarbons.

The greater reactivity of the isoolefins compared to the corresponding normal olefins, provides an excellent means of separating the two by formation of the isoethers and concurrent fractionation (distillation) of the resulting product stream according to the present invention whereby the unreacted normal olefin is removed as an overhead and the ether product is removed as a bottom.

However, by employing more severe conditions in the distillation column reactor the normal olefins can also be reacted to form ethers, there by producing greater quantities of ether for blending with gasoline stocks as octane improvers. The mixed isoether and normal ethers, need not be used just as octane improvers in gasoline, since the boiling points of the various isoethers and normal ethers are sufficiently different to allow subsequent fractionation to separate them.

The manner of operating the distillation column reactor, i.e., the severity of the conditions is easily determinable by the operator to obtain the desired result, i.e., react substantially only the isoolefin with the alcohol to separate the isoolefin and recover the normal olefin or maximize the etherification, by increasing the pressure in the range of 0 to 400 psig until the desired extent of reaction is obtained. Over this pressure range as discussed later, the temperature will generally be in the range of 10° to 135° C.

The ether products in the case of isobutene are tertiary butyl alkyl ether and isobutyl alkyl ether and similarly the products in the case of isoamylene are tertiary amyl alkyl ether and isoamyl alkyl ethers. The products in the case of normal butenes (butene-1 and butene-2) are normal butyl alkyl ether and secondary alkyl ether. The products in the case of normal amylenes are normal-amyl alkyl ether and secondary amyl alkyl ethers (2-amyl alkyl ether and 3-amyl alkyl ether).

In the embodiment where ether production is maximized the normal olefins may not, and generally will not be entirely converted to ethers. The process generally comprises (a) feeding a stream containing $C_4$ to $C_5$ olefins, preferably a mixture of either $C_4$ iso- and normal olefins or $C_5$ iso- and normal olefins to a distillation column reactor into a feed zone, (b) feeding a $C_1$ to $C_6$ alcohol into said feed zone, (c) concurrently: (1) contacting said olefin containing feed and the $C_1$ to $C_6$ alcohol with a fixed bed acid cation exchange resin, packing in a distillation reaction zone, thereby catalytically reacting at least a portion of the olefins with the alcohol to form an ether product and (2) fractionating the resulting mixture of ether product and unreacted feed, (d) withdrawing the ether product from the distillation column reactor at a point below said feed zone and (e) withdrawing the unreacted feed from the distillation column reactor a point above the feed zone, preferably above the acidic cation exchange resin.

Preferably the feed to distillation reactor is either a substantially $C_4$ or $C_5$ stream. There may be a mixture of olefins, i.e., iso and normal as well as the corresponding alkanes. The reaction can be carried out with either only the iso or normal olefin, however in such a case there would normally be a small amount, e.g., 0.5 to 15 mole % up to 25 or 30 mole % of a non reactive diluent present such as a normal alkane which has a lower boiling point than the ether product for control of the reaction. Since the alcohol is present, side reactions such as oligomerization of the olefins would be suppressed.

Where the ether product is a mixture of ethers and separation of the ethers is desired it would be the usual practice to remove the ether product to a separate column and fractionate it there. However, it would be possible to fractionate the ethers in the distillation column reactor by employing a longer column below the catalyst zone where the ethers could be fractionated and withdrawn at various points by side draws, as well as the bottoms removal.

One species of the present invention is a method for the preparation of methyl tertiary butyl ether from streams containing mixtures of isobutene and normal butenes.

The method of the invention for producing methyl tertiary ether comprises (a) feeding a mixture containing an isobutene and normal butene to a distillation column reactor into a feed zone, (b) feeding methanol into said feed zone (c) concurrently: (1) contacting said mixture and methanol with a fixed bed acidic cation exchange resin packing in a distillation-reaction zone, thereby catalytically reacting the isobutene with methanol to form methyl tertiary butyl ether, and (2) fractionating the resulting mixture of ether and normal olefin, (d) withdrawing the ether from the distillation column reactor at a point below said feed zone and (e) withdrawing the normal-olefin from the distillation column reactor at a point above the feed zone, preferably above the acidic cation exchange resin.

A particular embodiment of the present invention is a method for the separation of isobutene from a mixture comprising n-butene and isobutene. More generally, the invention is suitable for the separation of isobutene from a hydrocarbon stream which is substantially $C_4$ hydrocarbons, such as n-butene, isobutene, n-butene, isobutane, and butadiene (minor amounts of $C_3$ and $C_5$ hydrocarbons, i.e., less than 10% may be incidental components of such $C_4$ stream).

Briefly stated, the present method for separating isobutene comprises:

(a) feeding (1) a mixture containing isobutene and n-butene and (2) methanol to a distillation column reactor into a feed zone, (b) concurrently:

(1) contacting said mixture and methanol with a fixed bed acidic cation exchange resin packing in a distillation-reaction zone, thereby catalytically reacting isobutene with methanol to form methyl tertiary butyl ether, and (2) fractionating the resulting mixture comprising methyl tertiary butyl ether and n-butene, (c) withdrawing said methyl tertiary butyl ether from said distillation column reactor at a point below said feed zone and, (d) withdrawing n-butene from said distillation column reactor at a point above the feed zone.

The reaction system can be described as heterogeneous since the catalyst remains as a distinct entity. The catalyst may be employed in such conventional distillation packing shapes, as Raschig rings, Pall rings, saddles or the like. Similarly, the resin may be employed in a granular or bead form as described herein.

The alcohol, e.g., methanol may be and is preferably present in a stoichiometric amount although an excess of up to 10%, may be desirable. In addition, slightly less than a stoichiometric amount may be employed. It should be appreciated that the skilled chemist will optimize the proportions and precise conditions for each particular piece of equipment and variation in catalyst, once the basic invention is comprehended.

It has been found that the resin beads in a conventional fixed bed form too compact a mass for the upward flowing vapor and downward flowing liquid. However, it has been found that placing the resin beads into a plurality of pockets in a cloth belt, which is supported in the distillation column reactor by open mesh knitted stainless steel wire by twisting the two together, allows the requisite flows, prevents loss of catalyst, allows for the normal swelling of the beads and prevents the breakage of the beads through mechanical attribution. This novel catalyst arrangement is described in detail in copending, commonly owned U.S. Pat. No. 4,242,530 which is incorporated herein.

The cloth may be of any material which is not attacked by the hydrocarbon feed or products under the conditions of the reaction. Cotton or linen are useful, but fiber glass cloth or "Teflon" cloth are preferred. Briefly, a preferred catalyst system comprises a plurality of closed cloth pockets arranged and supported in said distillation column reactor by wire mesh intimately associated therewith.

The particular catalytic material may be a powder, small irregular fragments or chunks, small beads and the like. The particular form of the catalytic material in the cloth pockets is not critical, so long as sufficient surface area is provided to allow a reasonable reaction rate. This sizing of catalyst particles can be best determined for each catalytic material (since the porosity or available internal surface area will vary for different materials and of course affects the activity of the catalytic material).

What readily distinguishes the present method from the prior art is that the prior art has consistently employed a continuous liquid phase system for contacting the isoolefin with the acidic catalyst, whereas the present invention carries out the method in a catalyst packed distillation column which can be appreciated to contain a vapor phase and some liquid phase as in any distillation.

The etherification reaction of isobutene and the fractionation of the resultant n-butene-ether mixture is carried out simultaneously, i.e., concurrently. That is, as the ether is formed in the catalyst bed, the lower boiling n-butene is fractionated away in the catalyst bed and removed overhead while the high boiling ether drops to the lower portion of the column.

The bulk type liquid phase reactions of the prior art had as one problem the control of the temperature. The distillation avoids this problem entirely.

The Haunschild patents described above, were an improvement in that there was some etherification catalyst in the column, but the etherification and distillation were not concurrent. Etherification occurs only in the liquid phase in the downcomers with distillation occurring subsequently on the tray, thus teaching only a contact with the catalyst in the down flow of the reactants, which severely limited the reaction and prompted the patentee to suggest multiple conventional fixed bed reactions of isobutene and alcohol to form ether prior to introduction to various trays in the distillation column.

Another species of reaction, which is closely related to the MTBE production is the production of high purity isobutene from the dissociation of MTBE. This reaction is obtained by feeding MTBE to the catalyst bed packing in the reaction-distillation column, recovering methanol bottoms and high purity (95%+) isobutene overhead product, using the same acidic resin catalyst. The feed zone is the upper end of the catalyst bed.

In another closely related species of reaction, the reaction of methanol and isobutene is conducted as described herein, generally, but the amount of methanol is less than stoichiometric amount. By raising temperatures (e.g., increase the pressure in the column) and the dimerization of isobutene is favored. A bottoms product of high purity diisobutene (fewer codimers than in the usual type of process to produce dissobutene from $C_4$ streams) is obtained.

The streams containing the olefins to be etherified may be substantially pure olefin streams, such as isobutene, n-butenes, isoamylene or n-amylenes. As noted above, it would be desirable to have non-reactive diluents added in order to control the reaction. This is particularly the case where the stream is the isoolefin, since the isoolefins are so highly reactive. In the case of the normal olefins, the reaction is less vigorous and the unreacted normal olefin may serve as the diluent. The diluent serves not only to reduce the concentration, and hence the contact of the reactive olefins with the catalyst, but also as a means of heat removal from the reaction zone.

The principal current application of the present process of etherification is contemplated for the various $C_4$ and $C_5$ refinery streams, which will contain widely varying concentrations of normal olefins, isoolefins, normal alkanes and isoalkanes. Usually a $C_4$ stream is principally $C_4$ although there may be small amounts of residual $C_3$ and $C_5$ hydrocarbons usually less than 10 mole % and similarly the $C_5$ stream may contain correspondingly small amounts of residual $C_4$ and $C_6$ hydrocarbons.

One of the advantages of the present process is that it is effective to remove even very small amounts of olefins, particularly the isoolefins from the feed streams. For example, even in the case of normal olefins, the severity of the conditions could be increased, without effecting the non reactive alkane components of the stream. Economics and the volumes handled would be the limiting considerations where small amounts, e.g., less than 5 mole % of olefin were present in the stream.

Mixed $C_4$ streams containing principally isobutane (I-$C_4$), normal butane (n-$C_4$), butene (B-1), isobutene (I-B), trans butene-2 (TB-2) and cis butene-2 (CB-2) (plus some minor impurities including butadiene), can be treated with cold sulfuric acid to remove isobutene and produce a butylene concentrate.

It has been found that a distillation column packed with a properly supported acid catalyst into which the mixed $C_4$ stream and methanol are fed can produce a bottom stream containing methyl tertiary butyl ether and an overhead stream that is relatively free of isobutene.

The alcohols employed are those having 1 to 6 carbon atoms. Preferred are those having one hydroxyl group. Although those having two or more hydroxyl groups are operable the ether product becomes more complex and the likelihood of oligomers or even polymers is increased.

Preferred alcohols include methanol, ethanol, propanol, n-butanol, tertiary butanol, 1-pentanol, 2-pentanol, 3-pentanol, 1-hexanol, 2-hexanol, 3-hexanol, cyclopentetanol and hexanol. A preferred grouping of alcohols are those having 1 to 3 carbon atoms and one hydroxyl group.

The alcohols may be used alone or in mixtures of any proportion to produced highly complex ether products having unique properties as octane improvers for gasoline.

The olefin feed and the alcohol may be feed into the reaction zone separately or premixed and therein in a single stream.

The success of the catalytic distillation approach lies in an understanding of the principles associated with distillation. First, because the reaction is occurring concurrently with distillation, the initial reaction product, e.g., methyl tertiary butyl ether is removed from the reaction zone nearly as quickly as it is formed. This removal of the ether minimizes decomposition of the ether and chaining to form isobutene polymer. Second, because all the $C_4$ components are boiling, the temperature of the reaction is controlled by the boiling point of the $C_4$ mixture at the system pressure. The heat of reaction simply creates more boil up, but not increase in temperature. Third, the reaction has an increased driving force because the reaction products have been removed and can not contribute to a reverse reaction (LeChatelier's Principle).

As a result, a great deal of control over the rate of reaction and distribution of products can be achieved by regulating the system pressure. Also, adjusting the through-put (residence time=liquid hourly space velocity$^{-1}$) gives further control of product distribution and degree of isobutene removal and/or total olefin reaction.

The temperature in the reactor is determined by the boiling point of the $C_4$'s at any given pressure or in the case of any mixture of $C_4$'s or $C_5$'s with alcohol, the boiling point of the unreacted hydrocarbons. This, of course refers to the highest temperature in the column, i.e., the overhead, and the temperature in the lower portions of the column will reflect the constitution of the material in that part of the column, which will be lower than the overhead, that is, at constant pressure a change in the temperature of the system, indicates a change in the composition in the column. Thus, to change the temperature the pressure is changed. By increasing the pressure, the temperature in the system is increased. Generally, pressures in the range of 0 to 400 psig are or may be employed, preferably 30 to 150 psig. For the C$_4$ stream, the present reaction will be carried out generally at pressures in the range of 10 to 300 psig, which will generally mean temperatures in the range of 10° to 100° C.

The reaction of olefins, e.g., isobutene with alcohol, e.g., methanol is equilibrium limited; however, by carrying out the reaction in a distillation column reactor and fractionating the formed product, e.g., methyl tertiary butyl ether (MTBE), downward away from the reaction zone, the equilibrium is constantly disrupted and hence the reaction never comes to equilibrium. This has the advantage of course, of achieving an effective 100% conversion, provided the catalyst bed is of sufficient length such that none of the olefin, e.g., isobutene escapes therefrom to go overhead with the unreacted material, n-butenes (a problem the Haunschild process does not solve). The adjustment of the size of the catalyst bed is a mere mechanical step to be determined for each reactor and in accordance with the reaction conditions.

The ether system (e.g., MTBE) would normally be considered anhydrous; however, small amounts of water often saturate the feed stream and represent about 400 to 600 ppm thereof. The process will continue to operate in the same fashion, in the presence of this amount of water. Generally the system will be employed with less than 1 mole % water in the feed. However, the limitation on water is relevant to the ether reaction. Quite obviously, where water is a reactant or a principal component of a feed stream according to the generic invention, it may be present in substantially larger amounts as required.

The feed to the distillation column reactor is made at the lower end of the catalyst bed for the ether reaction, preferably into the catalyst to allow immediate contact of the isobutene and methanol with the catalyst which is characterized as the feed zone.

A reflux is preferably included in the system. The reflux ratio could vary over the rate of 1 to 20:1. In practice, the higher ratio may be used to compensate for a short catalyst bed such as required for experimental work. In commercial size units the catalyst bed would be provided so that lower reflux and hence higher unit productivity could be obtained.

Catalysts suitable for the new ether process are cation exchanges, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenylether and others. The polymers may be prepared in the presence of absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C. and the sulfuric acid should contain sufficient sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.25 to 1 mm, although particles from 0.15 mm up to about 1 mm may be employed. The finer catalysts provide high surface area, but also result in high pressure drops through the reactor. The macroreticular form of these catalysts is preferred because of the much larger surface area exposed and the limited swelling which all of these resins undergo in a non-aqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. No.'s 3,784,399; 3,770,567 and 3,849,243.

In addition to pockets of resin catalyst described, cattion exchange resin structures prepared by the process described in copending, commonly owned U.S. Pat. No. 4,250,052, which is incorporated herein, may be employed.

EXAMPLES

In the following examples*, the feed rate of C's to the column is adjusted to maintain a bottoms temperature which would correspond to low C$_4$ concentration. The catalyst employed was Amberlyst 15, manufactured by Rohm and Haas, Philadelphia, Pa.

| Component | Mole % |
|---|---|
| Isobutane | 2.8 |
| n-Butane | 8.6 |
| Butene-1 | 24.6 |
| Isobutene | 50.5 |
| Trans-butene-2 | 10.4 |
| Cis-butene-2 | 3.1 |
| Butadiene | .5 |
| ratio butene-1/butene-2 | 1.8 |

Examples 1, 2 and 3

The laboratory distillation-reactor column was a one inch diameter, five foot tall tube containing two feet of conventional glass 1/16 inch helices and three feet of the catalytic packing. The pilot column is 3 inches in diameter with 10 feet of catalyst packing and 5 feet of conventional ⅜ inch pall rings.

In the laboratory column used in these examples the bags are made in the form of a cloth belt approximately six inches wide with narrow pockets approximately ¾ inch wide sewn across the belt. The pockets are spaced about ¼ inch apart. These pockets are filled with the catalyst beads to form approximately cylindrical containers, and the open ends are then sewn closed to confine the beads. This belt is then twisted into a helical form to fit inside the one inch column. Twisted in with the belt is also a strip of an open mesh knitted stainless steel wire, which serves to separate the resin filled cloth pockets and provide a passage for vapor flow. A similar catalyst support system was used in the 3 inch pilot plant column.

The wire mesh provides the support for the catalyst (belt) and provides some degree of vapor passage through the catalyst beads, which otherwise form a very compact bed which has a high pressure drop. Thus, the down flowing liquid is in intimate contact with the rising vapors in the column.

In commercial-scale operations, it is contemplated, catalyst packing would be made up of alternating layers of resin-filled cloth belts similar to the ones described above, and a spacing material which could be of any convenient, suitable substance, such as a corrugated wire screen or wire cloth or a knitted wire mesh. The layers would be arranged vertically or horizontally. For simplicity of fabrication and for better distribution of vapor flow passages, a vertical orientation is preferred. The height of a section of this packing could be of any convenient dimension, from a few inches to several feet. For ease of assembly and installation, the packing would be made into sections of the desired shape and size, each section fastened together with circumferential bands of tie wires depending on its size and shape. A complete assembly in a column would consist of several sections, arranged in layers, with possibly the orientation of the resin-filled belts turned at right angles in successive layers to improve liquid and vapor flow distribution.

Other configurations which may be useful but with certain draw backs would be cages of wire cloth to contain catalyst beads, immersed in liquid on a conventional sieve tray. Disadvantages would be the restriction of vapor flow by the close weave of the wire, which may be compensated by allowing the beads to move freely in the cage, thereby causing attrition, Similarly, suspension of the catalyst on a tray would present problems of attrition, maintaining suspension and preventing catalyst from leaving the tray.

In operation, the isobutene containing $C_4$ feed and methanol enter through into the lower end of the catalytic zone which contains the catalyst bag belt as described. The temperature and pressure in the column are such that the $C_4$ and methanol boil up in the column, however, as the isobutene and alcohol contact the catalyst, ether is formed, which being higher boiling than the $C_4$ stream, passes to the bottom of the reactor where it is removed. Generally a portion is recovered through and another portion recycled into a reboiler and hence back into the bottom of the column.

Meanwhile, the n-butenes pass upward through the catalyst zone and out of the column to a condenser hence into an accumulator. In normal operation, a portion is recovered as butene concentrate and a portion is returned as reflux through into the column.

EXAMPLES 1, 2 AND 3

These runs illustrate MTBE production.

|  | Example | | |
|---|---|---|---|
|  | 1 | 2 | 3 |
|  | Laboratory Column | | Pilot Plant Column |
|  | $LHSV^{*-1}$ = 1.0 hr | | $LHSV^{-1}$ = 1.4 hr |
|  | 115g (190 ml) cat | | 2640g (4400 ml) cat |
| System pressure | 80 psig | | 100 psig |
| Temperature: | | | |
| Bottoms | 228° F. | | 260° F. |
| Middle cat. bed | 138° F. | | 160° F. |
| Methanol Feed | 2.5 ml/min | | 24 ml/min |
| Reactor | | | |
| Recovery Rate | | | |
| Overhead, grams/hr | 120 | — | 3060 ml/hr |
| Bottoms, grams/hr | 264 | — | 4980 ml/hr |
| Analysis, Mole % | | | |
| Overhead | | | |
| Isobutane | 6.1 | 6.6 | 6.1 |
| Normal butane | 18.0 | 15.5 | 15.8 |
| Butene-1 | 40.6 | 40.5 | 47.0 |
| Isobutene | 11.2 | 9.8 | 1.3 |
| Trans-butene-2 | 18.8 | 19.1 | 24.2 |
| Cis-butene-2 | 5.1 | 5.2 | 5.2 |
| Butadiene | .3 | .3 | .3 |
| Bottoms | | | |
| Methanol and $C_4$'s | 5.5 | 7.8 | 1.3 |
| Tertiary Butyl alcohol | 2.5 | .7 | .7 |
| Methyl teritary butyl ethyl (MTBE) | 93.2 | 91.2 | 91.9 |
| $C_8$'S and heavier | .8 | .3 | 6.1 |

*$LHSV^{-1}$ calculated by dividing overhead take-off rate into the volume of resin in the catalytic zone.

The process operated according to the present invention gives excellent yields of MTBE at a reasonable feed rate.

EXAMPLES 4 AND 5

These examples illustrate the production of high purity isobutene from methyl tertiary butyl ether. The one inch laboratory column was used and packed with 72 grams of catalyst distillation packing as described in pockets of a cloth belt. The catalyst was in the lower portion of the column for this reaction and the feed (MTBE) was at the upper end of the catalyst bed. Two runs were made using two different purities of feed. The conditions and results are set out below:

|  | Example | |
|---|---|---|
|  | 4 | 5 |
| Feed mole % MTBE | 95.6% | 99.1% |
| Recovery Rate | | |
| Overhead ml/hr | 100 | 100 |
| Bottom | not recorded | not recorded |
| Pressure, psig | 70 | 80 |
| Temperature, °F. | | |
| Overhead | 118 | 122 |
| Bottoms | 212 | 220 |
| Middle cat. bed | 214 | 217 |
| Analysis, %* | | |
| Overhead | | |
| Isobutane | .02 | .05 |
| Normal butane | .4 | .01 |
| Butene-1 | .5 | .05 |
| Isobutene | 96.5 | 99.6 |
| Trans-butene-2 | 1.6 | .2 |
| Cis-butene-2 | .9 | 1.2 |
| Butadiene | .03 | .01 |
| Bottom | mixture of MTBE and methanol | mixture of MTBE and methanol |

*gas phase chromatography area

EXAMPLES 6, 7 AND 8

Example 6 illustrates the flexibility of the present process to produce high purity diisobutene from the reaction of methanol and isobutene or MTBE only. The three inch pilot column was used. In Example 7 the column was modified by adding an additional 5 feet of column. In example 6, the column contained 5 feet of conventional Pall rings in the lower portion and 10 feet of the catalyst in cloth bags in the upper portion. In Example 7, an additional 2.5 feet of catalyst packing was added and 2.5 feet of ¼ inch conventional saddles on top of that. In both runs, methanol was fed at the top of the catalyst bed and the $C_4$ feed (as described above) was fed below the catalyst bed. The feed rates were adjusted to obtain the desired product distribution.

In example 8, high purity methyl tertiary butyl ether (99%) was the feed to column as employed in Example 7. The MTBE was fed into the column at the bottom of the catalyst bed. There was essentially no overhead removed except that necessary for analysis. The example demonstrates a unique method for producing diisobutene having a very low codimer contamination. The condition and results of the runs are described below:

|  | Example |  |  |
|---|---|---|---|
|  | 6** | 7 | 8 |
| Rate of Recovery |  |  |  |
| Overhead, liters/hr | 4.5 | 3.0 | essentially 0 |
| Bottoms, liters/hr | 4.5 | 4.2 | 4.5 |
| Pressure, psig | 100 | 120 | 78 |
| Temperature °F. |  |  |  |
| Overhead | 155 | 158 | 82 |
| Bottoms | 350 | 260 | 245 |
| Middle Cat. bed | 180 | 165 | 220 |
| Analysis %* |  |  |  |
| Overhead |  |  |  |
| Isobutane | 6.5 | 6.2 | — |
| Normal butane | 17.0 | 17.0 | 1.5 |
| Butene-1 | 32.2 | 46.9 | .8 |
| Isobutene | 6.2 | trace | 69.6 |
| Trans-butene-2 | 28.5 | 24.2 | .4 |
| Cis butene-2 | 9.4 | 5.0 | — |
| Butadiene | .2 | .6 | — |
| Dimethyl ether |  |  | 27.7 |
| Bottoms |  |  |  |
| Lights, methanol | .3 | 3.2 | .6 |
| Tertiary butyl alcohol |  | 1.0 | 5.1 |
| MTBE | 32.9 | 95.6 | 68.7 |
| Unknown ether*** | 2.2 |  | .1 |
| Isobutene |  |  |  |
| 2,4,4-Trimethyl pentene-1 | 40.2 |  | 17.6 |
| 2,4,4-Trimethyl pentene-2 | 10.5 |  | 5.3 |
| Codimers | 7.1 |  | .1 |
| Back flush heavies | 7.0 | .2 | 2.4 |
| Triisobutene |  |  |  |

*gas phase chromatography area
**reduced methanol below stoichiometric amount
***isobutyl methyl ether

EXAMPLE 9

This work was carried out on the 3 inch pilot plant column (Example 3). The pressure was 220 psig. The feed was a commercial $C_4$ stream of the following analysis:

|  | wt. % |
|---|---|
| Propane ($C_3$) | .2 |
| Propene ($C_3^=$) | .3 |
| Isobutane ($IC_4$) | 3.3 |
| Normal butane ($nC_4$) | 24.8 |
| Butene-1 (B-1) | 29.8 |
| Isobutene (IB) | 25.2 |
| Trans butene-2(t-B-2) | 12.7 |
| Cis butene-2(c-B-2) | 3.4 |
| Butadiene | .2 |
|  | 99.9 |

The feed rate of the $C_4$ stream was about 170 grams/min. and the methanol 27 grams/min. The run was carried out for 6½ hours and the results are those existing at the end of the run. The temperature of the overhead was 196° F. and the bottoms 308° F. The temperature in the reaction zone (catalyst zone) from bottom to top was 211°-197° F.

The alcohol was fed at the top of the catalyst bed (reaction zone) and the $C_4$ stream into the lower portion of the reaction zone.

The analysis was carried out in a 40 foot glass capillary column packed with SE 30 using helium as a carrier.

| Product analysis: |  |
|---|---|
| Component | wt. % |
| Overhead: |  |
| Lights | .11 |
| $C_3$ | .36 |
| $C_3^=$ | .59 |
| $IC_4$ | 4.9 |
| $nC_4$ | 30.1 |
| B-1 | 36.4 |
| IB | 1.1 |
| t-B-2 | 17.2 |
| c-B-2 | 5.3 |
| BD | .3 |
| Heavies | 3.6 |
| Bottoms: |  |
| Methanol & C |  |
| Tertiary butyl alcohol | .39 |
| MTBE | 99.4 |
| Methyl secondary butyl ether (MSBE) | .30 |
| Methyl isobutyl ether (MIBE) | 1.15 |
| Methyl normal butyl ether (MNBE) | 0.49 |
| Heavies | .7 |

The physical limitation of the equipment prevented greater pressure and higher yields of the ethers of n-butenes, however the production of both MSBE and MNBE demonstrates the etherification of the normal butenes in accordance with the invention.

EXAMPLE 10

Using the 3 inch reactor described in Example 3 and the same feed as in Example 9, a feed of standard denatured alcohol* at about 4.9 pounds per hour and $C_4$ stream at 17.5 pounds per hour was fed to the column for 8 hours. The temperature of the overhead was 156° F. and the bottoms, 300° F. The temperature in the reaction zone (catalyst bed) from top to bottom was about 158°-172° F. with the alcohol fed at the top of the catalyst bed and the $C_4$'s into the lower portion of the reaction zone.

*Denaturants comprise 0.9 pounds per hour (about 18% of feed)

The product analysis was carried out in a 40 foot glass capillary column packed with SE 30 using helium as a carrier.

| Product Analysis: | |
|---|---|
| Component | wt. % |
| Overhead: | |
| Lights | .04 |
| $C_3$ | .25 |
| $C_3=$ | .41 |
| $IC_4$ | .46 |
| $nC_4$ | 30.8 |
| B-1 | 37.0 |
| IB | 3.4 |
| t-B-2 | 16.8 |
| c-B-2 | 4.8 |
| BD | .3 |
| Heavies | 1.5 |
| Bottoms | |
| $C_4$'s | 2.6 |
| Ethanol | 7.4 |
| MTBE | 8.2 |
| Unknown 1 | 1.6 |
| ETBE* | 79.4 |
| Unknown 2 | .5 |
| Unknown 3 | .4 |

*Ethyl Tertiary Butyl Ether

The invention claimed is:

1. A process for reacting $C_4$ and $C_5$ olefins with $C_1$ to $C_6$ alcohols to produce the corresponding ethers comprising
   (a) feeding a stream containing $C_4$ to $C_5$ olefins or a mixture thereof to a distillation column reactor into a feed zone,
   (b) feeding alcohol having one to six carbon atoms or mixtures thereof in said feed zone,
   (c) concurrently:
      (1) contacting said stream containing said olefins and said alcohol with a fixed bed acidic cation exchange resin packing in a distillation reaction zone thereby catalytically reacting at least a portion of said olefins and said alcohol to form an ether product and
      (2) fractionating the resultant ether product from unreacted materials,
   (d) withdrawing the ether from the distillation column reactor at a point below said feed zone, and
   (e) withdrawing unreacted materials from the distillation column reactor at a point above said feed zone.

2. The process according to claim 1 wherein said olefins are $C_4$ olefins and said stream contains inert hydrocarbon diluent having a boiling point lower than the ether product.

3. The process according to claim 2 wherein said diluent comprises 5 to 15 mole % of said stream.

4. The process according to claim 2 wherein said olefins are isobutene.

5. The process according to claim 2 wherein said olefins are n-butenes.

6. The process according to claim 2 wherein said olefins are a mixture of isobutene and n-butenes.

7. The process according to claim 2 wherein said diluent is $C_4$ alkanes.

8. The process according to claim 1 wherein said olefins are $C_5$ olefins and said stream contains inert hydrocarbon diluent having a boiling point lower than the ether product.

9. The process according to claim 8 wherein said diluent comprises 5 to 15 mole % of said stream.

10. The process according to claim 8 wherein said olefins are isoamylene.

11. The process according to claim 8 wherein said olefins are n-amylenes.

12. The process according to claim 8 wherein said olefins are a mixture of isoamylene and n-amylenes.

13. The process according to claim 8 wherein said diluent is $C_4$ alkanes.

14. The process according to claim 1, 2, 4, 5, 6, 8, 10, 11 or 12 wherein said alcohol has one hydroxyl group.

15. The process according to claim 14 wherein said alcohol has 1 to 3 carbon atoms.

16. The process according to claim 1 wherein said ether product is withdrawn below said resin packing and said unreacted materials are withdrawn above said resin packing.

17. The process according to claim 14 wherein said alcohol is methanol, ethanol or propanol.

18. The process according to claim 17 wherein said alcohol is ethanol.

19. The process according to claim 17 wherein said alcohol is propanol.

20. The process according to claim 17 wherein said alcohol is a mixture of ethanol and methanol.

21. The process according to claim 1 wherein the temperature in the column is the boiling point of the unreacted hydrocarbons and alcohol in said column under the pressure in said column.

22. The process according to claim 21 wherein the reaction and fractionation are carried out at a pressure in the range of 0 to 400 psig.

23. The process according to claim 22 where the pressure is in the range of 10 to 300 psig.

24. The process according to claim 6 wherein said contacting and reacting of olefins and alcohol are carried out to react substantially only isobutene with said alcohol.

25. The process according to claim 6 wherein said contacting and reacting of olefins and alcohol are carried out to react both isobutene and n-butenes with said alcohol.

26. The process according to claim 12 wherein said contacting and reacting of olefins and alcohol are carried out to react substantially only isoamylene with said alcohol.

27. The process according to claim 12 wherein said contacting and reacting of olefins and alcohol are carried out to react both isoamylene and n-amylenes with said alcohol.

28. A method of producing tertiary butyl alkyl ether and mixtures thereof with isobutyl alkyl ether or butyl alkyl ether, comprising:
   (a) feeding:
      (1) a mixture containing isobutene and normal butene and
      (2) alcohol having 1 to 6 carbon atoms to a distillation column reactor into a feed zone,
   (b) concurrently:
      (1) contact said mixture and said alcohol with a fixed bed acid cation exchange resin packing in a distillation reaction zone thereby catalytically reacting at least the isobutene to form an ether product containing tertiary butyl alkyl ether or a mixture thereof with butyl alkyl ether or isobutyl alkyl ether,
      (2) fractionating the resulting mixture of ether product and unreacted materials, (c) withdrawing the ether product from the distillation column reactor at a point below said feed zone, and (d) withdrawing the unreacted materials from the distillation column reactor at a point above said feed zone.

29. The method according to claim 28 wherein the ether product is substantially the reaction product of tertiary butene and said alcohol and the unreacted material comprises substantially n-butenes in said feed mixture.

30. The method according to claim 29 wherein the ether product is substantially tertiary butyl alkyl ether with some isobutyl alkyl ether present.

31. The method according to claim 29 wherein the ether product is a mixture of tertiary butyl alkyl ether, isobutyl alkyl ether and butyl alkyl ether and the unreacted material comprises a portion of the n-butenes.

32. The method according to claim 28, 29 or 32 wherein the alcohol has one hydroxyl group.

33. The method according to claim 32 wherein the alcohol has 1 to 3 carbon atoms.

34. The method according to claim 33 wherein the alcohol is ethanol.

35. The method according to claim 33 wherein the alcohol is propanol.

36. The method according to claim 33 wherein the alcohol is a mixture of methanol and ethanol.

37. A method of producing tertiary amyl alkyl ether and mixtures thereof with isoamyl alkyl ether, or amyl alkyl ether comprising:

(a) feeding:
(1) a mixture containing isoamylene and normal amylene and
(2) alcohol having 1 to 6 carbon atoms to a distillation column reactor into a feed zone, (b) concurrently:
(1) contacting said mixture and said alcohol with a fixed bed acid cation exchange resin packing in a distillation reaction zone thereby catalytically reacting at least the isoamylene to form an ether product containing tertiary amyl alkyl ether or a mixture thereof with isoamyl alkyl ether or amyl alkyl ether, (2) fractionating the resulting mixture of ether product and unreacted materials, (c) withdrawing the ether product from the distillation column reactor at a point below said feed zone, and (d) withdrawing the unreacted materials from the distillation column reactor at a point above said feed zone.

38. The method according to claim 37 wherein the ether product is substantially the reaction product of tertiary amylene and said alcohol and the unreacted material comprises substantially n-amylenes in said feed mixture.

39. The method according to claim 38 wherein the ether product is substantially tertiary amyl alkyl ether with some isoamyl alkyl ether present.

40. The method according to claim 37 wherein the ether product is a mixture of tertiary amyl alkyl ether, isoamyl alkyl ethers and amyl alkyl ethers and the unreacted material comprises a portion of the n-amylene, 41. The method according to claims 37 or 38 wherein the alcohol has one hydroxyl group.

42. The method according to claim 41 wherein the alcohol has 1 to 3 carbon atoms.

43. The method according to claim 42 wherein the alcohol is methanol.

44. The method according to claim 42 wherein the alcohol is ethanol.

45. The method according to claim 42 wherein the alcohol is propanol.

46. The method according to claim 42 wherein the alcohol is a mixture of methanol and ethanol.

47. The method according to claim 31 wherein said butyl alkyl ethers comprises alkyl normal butyl ether and alkyl secondary butyl ether.

48. The method according to claim 40 wherein said amyl alkyl ethers comprises alkyl normal amyl ether and alkyl secondary amyl ethers.

* * * * *

UNITED STATES PATENT AND TRADEMARK OFFICE
CERTIFICATE OF CORRECTION

PATENT NO. : 4,336,407
DATED : June 22, 1982
INVENTOR(S) : Lawrence A. Smith, Jr.

It is certified that error appears in the above—identified patent and that said Letters Patent is hereby corrected as shown below:

Column 8, line 59 reads

"highest", but should read -- lowest --

Column 8, line 63 reads "lower", but should read
--higher--

Signed and Sealed this

Sixteenth Day of November 1982

[SEAL]

Attest:

GERALD J. MOSSINGHOFF

Attesting Officer     Commissioner of Patents and Trademarks